(12) United States Patent
Poole et al.

(10) Patent No.: US 8,841,132 B2
(45) Date of Patent: *Sep. 23, 2014

(54) METHOD FOR DETECTING COMPOUNDS CONTAINING SULFENIC ACID USING A 1,3-CYCLOHEXANEDIONE-BASED PROBE

(71) Applicant: Wake Forest University Health Sciences, Winston-Salem, NC (US)

(72) Inventors: Leslie B. Poole, Tobaccoville, NC (US); S. Bruce King, Walnut Cove, NC (US); Jacquelyn S. Fetrow, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/920,989

(22) Filed: Jun. 18, 2013

(65) Prior Publication Data

US 2013/0288268 A1 Oct. 31, 2013

Related U.S. Application Data

(60) Continuation of application No. 12/861,529, filed on Aug. 23, 2010, now Pat. No. 8,486,642, which is a division of application No. 11/863,413, filed on Sep. 28, 2007, now Pat. No. 7,803,630, which is a continuation of application No. 11/247,045, filed on Oct. 11, 2005, now Pat. No. 7,294,748.

(60) Provisional application No. 60/620,263, filed on Oct. 19, 2004.

(51) Int. Cl.
| | |
|---|---|
| *G01N 33/68* | (2006.01) |
| *G01N 33/52* | (2006.01) |
| *G01N 21/64* | (2006.01) |
| *G01N 33/574* | (2006.01) |

(52) U.S. Cl.
CPC ............ *G01N 33/68* (2013.01); *G01N 33/6815* (2013.01); *G01N 21/6428* (2013.01); *G01N 33/574* (2013.01)
USPC ............................. 436/120; 436/86; 436/172

(58) Field of Classification Search
CPC ....................... G01N 33/6818; G01N 21/6428
See application file for complete search history.

(56) References Cited

FOREIGN PATENT DOCUMENTS

DE 24 37 983 2/1976

OTHER PUBLICATIONS

Berry et al., Direct 4-Alkylation of 1,3-cyclohexamediones via Dianionic Species, Synthesis, 6:476-480 (1986).

(Continued)

*Primary Examiner* — Yelena G Gakh
*Assistant Examiner* — Michelle Adams
(74) *Attorney, Agent, or Firm* — Myers Bigel Sibley & Sajovec, P.A.

(57) ABSTRACT

The present invention provides compounds of Formula I:

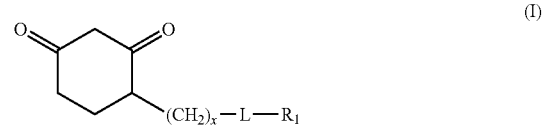

(I)

wherein: $R_1$ is a label (e.g., a detectable group and an antitumor agent); L is present or absent and when present is a linking group; and x represents an integer from 1 to 10; or a pharmaceutically acceptable salt thereof. The compounds are useful for, among other things, identifying cysteine sulfenic acids in proteins and monitoring oxidative damage in proteins and cells. Adduct formation can be detected using analytical methods such as electrospray ionization mass spectrometry and fluorescence.

13 Claims, 1 Drawing Sheet

(56) References Cited

OTHER PUBLICATIONS

Cole, K.P. et al., Intramolecular Formal oxa-[3+3] Cycloaddition Approach to the ABD System of Phomactin A, Org. Lett., vol. 5, No. 25, 2003, 4843-4846.

Ellis, Holly R., Novel Application of 7-Chloro-4-nitrobenzo-2-oxa-1,3-diazole To Identify Cysteine Sulfenic Acid in the AhpC Component of Alkyl Hydroperoxide Reductase. Biochemistry, 36, 15013-15018 (1997).

International Search Report and Written Opinion for PCT/US05/36502, date of mailing Mar. 7, 2007.

Kende, A.S. et al., The Stork-Danheiser Kinetic Alkylation Procedure: 3-Ethoxy-6-Methyl-2-Cyclohexen-1-one, Organic Syntheses, Coll. vol. 7, p. 208 (1990); vol. 64, p. 68 (1986).

Poole, Leslie B., Measurement of Protein Sulfenic Acid Content, Current Protocols in Toxicology, 17.2.1-17.2.21, John Wiley & Sons, Inc. (2003).

Poole, Leslie B., Identification of Cysteine Sulfenic Acid in AhpC of Alkyl hydroperoxide Reductase, Methods in Enzymology, vol. 348, p. 122-136 (2002).

Laboratory Safety Guidance OSHA 3404-11R(2011)pp. 1-50.

29 CFR § 1910.1450, Occupational exposure to hazardous chemicals in laboratories, pp. 599-613, (2012).

29 CFR § 1910.132, Subpart 1-Personal Protective Equipment pp. 416-417, (2009).

METHOD FOR DETECTING COMPOUNDS CONTAINING SULFENIC ACID USING A 1,3-CYCLOHEXANEDIONE-BASED PROBE

RELATED APPLICATIONS

This application is a continuation of and claims priority to U.S. application Ser. No. 12/861,529, filed Aug. 23, 2010, which is a divisional of and claims priority to U.S. patent application Ser. No. 11/863,413, filed Sept. 28, 2007, now U.S. Pat. No. 7,803,630, which is a continuation of U.S. patent application Ser. No. 11/247,045, filed Oct. 11, 2005, now U.S. Pat. No. 7,294,748, which claims the benefit of U.S. Provisional Patent Application Ser. No. 60/620,263, filed Oct. 19, 2004, the disclosure of each of which is incorporated by reference herein in its-entirety.

FIELD OF THE INVENTION

The present invention concerns compounds useful for labeling, detecting and isolating sulfenic acid-containing proteins and other molecules, and methods of making the same.

BACKGROUND OF THE INVENTION

Interest in the identification of cysteine sulfenic acids (R—SOH) in proteins by biochemists has grown substantially over the last decade as their biological roles in redox regulation and catalysis within an array of cellular proteins have become better defined (1,2). In spite of their importance, only a limited set of tools to identify these species are available, and most of these are only applicable to in vitro studies of pure, isolated proteins (3,4). Chemical modification of cysteine sulfenic acids by dimedone (5,5-dimethyl-1,3-cyclohexanedione) provides a useful way to "tag" these species with a specific, irreversible alkylating agent, but the lack of any spectral signal or label associated with the dimedone requires that the detection of this tag be undertaken by mass spectrometry (4-7).

SUMMARY OF THE INVENTION

Sulfenic acids such as cysteine sulfenic acids in compounds such as proteins can be identified by their ability to form adducts with dimedone, but this reagent imparts no spectral or affinity tag to the adduct to readily provide for subsequent analyses of such tagged proteins. Because 1,3-cyclohexanedione showed at least equivalent reactivity toward cysteine sulfenic acids, this compound was used as the basis for a synthetic procedure designed to add a functional group, an alcohol, then link fluorophores or biotin through this sidechain. The resulting compounds retain reactivity and specificity toward cysteine sulfenic acids in proteins, allowing for incorporation of the fluorescent or affinity label into the protein. Such compounds are useful for labeling proteins or other molecules containing sulfenic acids. More particularly, such compounds are useful for labeling sulfenic acids in proteins for their detection and isolation from complex protein mixtures, for quality control purposes, for detection and isolation of proteins in the course of experimental procedures, as a therapeutic agent to modulate cell signaling and other biological pathways, to evaluate the "redox status" of cells through a "fingerprint" of protein oxidation status linked with establishing the distinct patterns and extents of cellular changes due to particular treatments, and for the industrial purification of proteins for subsequent commercial purposes.

When conjugated to an antitumor agent, the compounds of the present invention are useful in the treatment of cancers such as breast, colon, lung, prostate, brain or liver cancer.

DETAILED DESCRIPTION OF THE PREFERRED EMBODIMENTS

Figure 1:
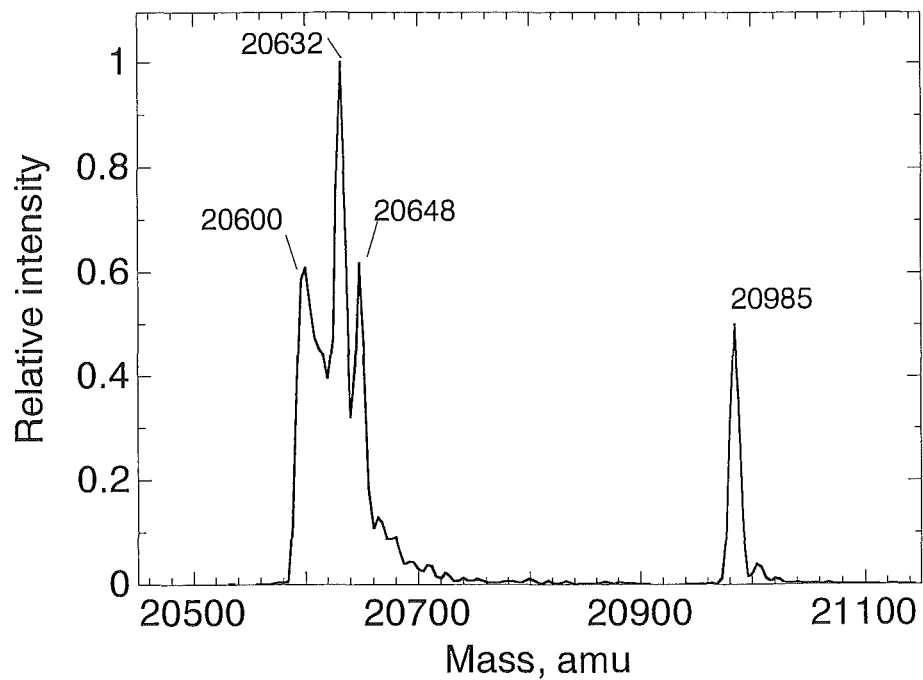
FIG. 1. Electrospray ionization mass spectrometry analysis of adducts with the sulfenic acid form of C165S AhpC. The mutant of the bacterial peroxidase AhpC (C165S) containing only the peroxidatic cysteine (Cys46) but not the resolving cysteine (Cys165) that participates in disulfide bond formation was treated with hydrogen peroxide to yield the relatively stabilized sulfenic acid form of the protein under anaerobic conditions, then incubated with 3-(2,4-dioxocyclohexyl)propyl 7-methoxy-2-oxo-2H-chromen-3-yl-carbamate (DCP-MCC, compound 7) to yield the covalent protein adduct. Shown are the transformed data that represent the relative abundance (shown as both the predicted and observed masses) of four prominent species of C165S AhpC: the protein with the active site Cys46 in the thiol (20,600 amu), sulfinic acid (20,632 amu), or sulfonic acid (20,648 amu) states, or in a covalent complex with DCP-MCC (20, 985 amu).

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

"Label" as used herein may be any suitable label or detectable or otherwise functional group, including but not limited to biotin, avidin, fluorophores, antigens (including proteins and peptides), antibodies, porphyrins, radioactive or stable isotopes, and (in some embodiments) anti-tumor or other therapeutic agents.

"Anti-tumor agent" as used herein may be any suitable anti-tumor agent, including but not limited to vinca alkaloids, epipodophyllotoxins, anthracycline antibiotics, actinomycin D, plicamycin, puromycin, gramicidin D, paclitaxel (TAXOL®, Bristol Myers Squibb), colchicine, cytochalasin B, emetine, maytansine, and amsacrine (or "mAMSA"). The vinca alkaloid class is described in *Goodman and Gilman's The Pharmacological Basis of Therapeutics*, 1277-1280 (7th ed. 1985) (hereafter "Goodman and Gilman"). Exemplary of vinca alkaloids are vincristine, vinblastine, and vindesine. The epipodophyllotoxin class is described in Goodman and Gilman, supra at 1280-1281. Exemplary of epipodophyllotoxins are etoposide, etoposide orthoquinone, and teniposide. The anthracycline antibiotic class is described in Goodman and Gilman, supra at 1283-1285. Exemplary of anthracycline antibiotics are daunorubicin, doxorubicin, mitoxantraone, and bisanthrene. Actinomycin D, also called Dactinomycin, is described in Goodman and Gilman, supra at 1281-1283. Plicamycin, also called mithramycin, is described in Goodman and Gilman, supra at 1287-1288. Additional chemotherapeutic agents include cisplatin (PLATINOL® Bristol Myers Squibb); carboplatin (PARAPLATIN®, Bristol Myers Squibb); mitomycin (MUTAMYCIN,® Bristol Myers Squibb); altretamine (HEXALEN®, U.S. Bioscience, Inc.); cyclophosphamide (CYTOXAN®, Bristol Myers Squibb); lomustine [CCNU] (CEENU®, Bristol Myers Squibb); carmustine [BCNU] (BICNU®, Bristol Myers Squibb); irinotecan (CPT-11). Additional examples of therapeutic or antitumor agents that may be used to carry out the present invention include but are not limited to those described in U.S. Patent Application Publication No. 2005/0181977, the disclosure of which is incorporated by reference herein in its entirety.

"Fluorophore" as used herein includes any suitable fluorophore, including but not limited to 2-(methylamino)benzoic acid (N-methylanthranilic acid), 7-methoxycoumarin-3-carbamate, or fluorescein.

"Linker" or "linking group" as used herein may be any suitable linking group, including but not limited to groups comprising, consisting of or consisting essentially of C, O, N, P and/or S (e.g., including H where necessary). In some embodiments the linker is not shown in generic structures as the linker may be thought of as a portion of the label.

Subjects, tissues, cells, cell fractions, and proteins utilized to carry out the present invention may be of any suitable source including microbial (including gram negative and gram positive bacteria, yeast, algae, fungi, protozoa, and viral, etc.), plant (including both monocots and dicots) and animal (including mammalian, avian, reptile, and amphibian species, etc.). Mammalian subjects include both humans and other animal species treated for veterinary purposes (including but not limited to monkeys, dogs, cats, cattle, horses, sheep, rats, mice, rabbits, goats, etc.)

The present invention provides compounds of Formula I:

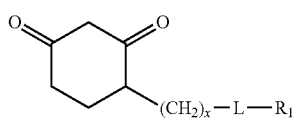

(I)

wherein:
$R_1$ is a label;
L is present or absent and when present is a linking group; and
x represents an integer from 1 to 10.

Compounds of Formula I may be synthesized by: reacting the anion of 3-ethoxy-2-cyclohexen-1-one with a protected halo lower alkyl alcohol [such as t-butyldimethylsilyl (tBDMS) protected halo lower alkyl alcohol; most particularly 3-iodo-1-propanol] in a suitable organic solvent (such as tetrahydrofuran) and hexamethylphosphoramide to form a 6-lower alkyl-OtBDMS-3-ethoxy-2-cyclohexen-1-one solution, adding an ammonium fluoride (such as tetrabutyl ammonium fluoride (TBAF)) to said solution to form an alcohol solution, adding a label to the alcohol solution, and adding HC1 to create a ketone at the (C)3 position.

Methods of Use. In general, the present invention provides a method of detecting a sulfenic acid containing target compound, comprising: contacting a compound as described herein (a compound of Formula I) with a target compound; and then detecting the presence or absence of binding of said compound to said target compound; the presence of binding indicating said target compound is a sulfenic acid containing compound. The method can be carried out in vitro or in vivo (e.g., where the compound is administered to a subject as described below) in accordance with known techniques or variations of such techniques that will be apparent to those skilled in the art given the present disclosure. When carried out in vitro the method can be performed on tissues, cells, cell-lysates or cell fractions, mixtures of compounds or individual compounds that are subject to or susceptible to the formation of sulfenic acids. The method can be utilized to determine whether a sulfenic acid containing target compound is present or absent from a sample suspected of containing the same. The method can be utilized to monitor redox signaling pathways and networks in cells and tissues in vitro. In specific embodiments the method can be utilized to identify cysteine sulfenic acids in a protein and/or monitor oxidative damage in proteins or cells. The method can be used to detect the formation of sulfenic acids in compounds such as proteins, including cysteine-containing proteins, when exposed to oxidants or oxidizing agents. The methods of the invention are useful for screening cells or tissue for exposure to environmental contaminants (particularly oxidative contaminants) or oxidative stress for diagnostic and forensic applications. For example, environmental toxins such as cigarette smoke (containing, e.g., benzo-a-pyrene) or automobile exhaust (with various oxides of nitrogen or sulfur, or with carbon monoxide), or chemotherapeutic agents such as cisplatin, can cause oxidative damage to cells which can be assessed by assays for sulfenic acid generation conducted in the methods described herein. Further, many chemotherapeutic agents work through induction of apoptosis in cancer cells that occurs through a redox signaling mechanism that can be discovered, or potentially manipulated, through the above assays. In addition, ischemia-reperfusion injury during the transient blockage of blood vessels (as in strokes or heart attacks) or as occurs with transplanted organs also imparts oxidative damage, all of which can be assessed through imaging approaches or at the level of their molecular details through the forementioned assays. Still further, exposure to radiation, including ionizing radiation, can be monitored or detected by detecting the formation of, or increased numbers of, sulfenic acids in cells, tissues, or proteins exposed or thought to be exposed to such radiation (e.g., a cell or tissue sample from an individual subject).

The methods of the invention can be implemented with any suitable assay format, including but not limited to: (α) visualization of sulfenic acid amount and location in intact tissues or cells, in permeabilized cells, or in fixed tissues or cells; and (b) detection, isolation and identification of molecules which are labeled based on their sulfenic acid content by applying the label top intact cells or tissues including using perfusion in anaesthetized animals), or to cell lysates, or to fractionated cell extracts, then isolating, detecting and identifying labeled proteins using chromatographic procedures, immunoaffinity procedures and/or two-dimensional gel procedures for separation followed by mass spectrometry or Western blot analysis for identification of labeled components.

A further aspect of the present invention is a method of labeling, detecting and/or isolating cysteine sulfenic acids in proteins, or peptides containing cysteine sulfenic acids, or small molecules containing sulfenic acids, comprising: applying a spectral or affinity tag to the sulfenic acid-containing compound, wherein the spectral or affinity tag is a compound as described herein (particularly compounds of Formulas I, II, and III herein). The applying step may be carried out by adding said compound to a composition (e.g., a solution, suspension, emulsion, multi-phase mixture etc.) comprising said compound, alone or in combination with other compounds, to a said composition, and then separating protein or labeled small molecule from free compound, and detecting the presence or absence of label on the protein in accordance with known techniques suitable for the particular label employed.

A further aspect of the present invention is a method, for monitoring or modulating protein or cellular oxidative damage, potentially in combination with detection of protein phosphorylation or other post-translational modifications in a protein, of cysteine residues of said protein, or in other molecules within a cell, comprising: reacting a spectral or affinity tag with a protein containing cysteine residues, wherein the spectral or affinity tag is a compound as described herein, and then measuring the activity of the labeled cysteine (e.g., by measuring the amount of label on the protein or cysteine in accordance with known techniques). Such methods may be carried out in like manner as described above. Similar methods may be used to monitor oxidative damage to cellular components in intact or permeabilized cells as well. Following incubation with the labeling reagent, unreacted reagent could be removed and cells imaged to quantify the level of incorporation of the label into cellular components. Additionally, cells subjected to the labeling agent could be disrupted for the analysis or isolation of labeled components as described above.

Linking Groups. Linking groups that may be used to form covalent conjugates of two functional moieties are known in the art. See, e.g., U.S. Pat. Nos. 6,420,377; 6,593,334; and 6,624,317. The specific linking group employed will depend upon the particular synthetic method used to make the covalent conjugate, as will be appreciated by those skilled in the art. A suitable linking group will permit the joining of groups to provide a metabolically stable conjugate. In general, the linking moiety may comprise an aliphatic, aromatic, or mixed aliphatic and aromatic group (e.g., alkyl, aryl, alkylaryl, etc.) and contain one or more amino acids or hetero atoms such as N, O, S, etc. For example, the linking group L may be a compound of the formula $-L_a-L_b-$, where $L_b$ is present or absent and $L_a$ and $L_b$ are each independently selected from the group consisting of:

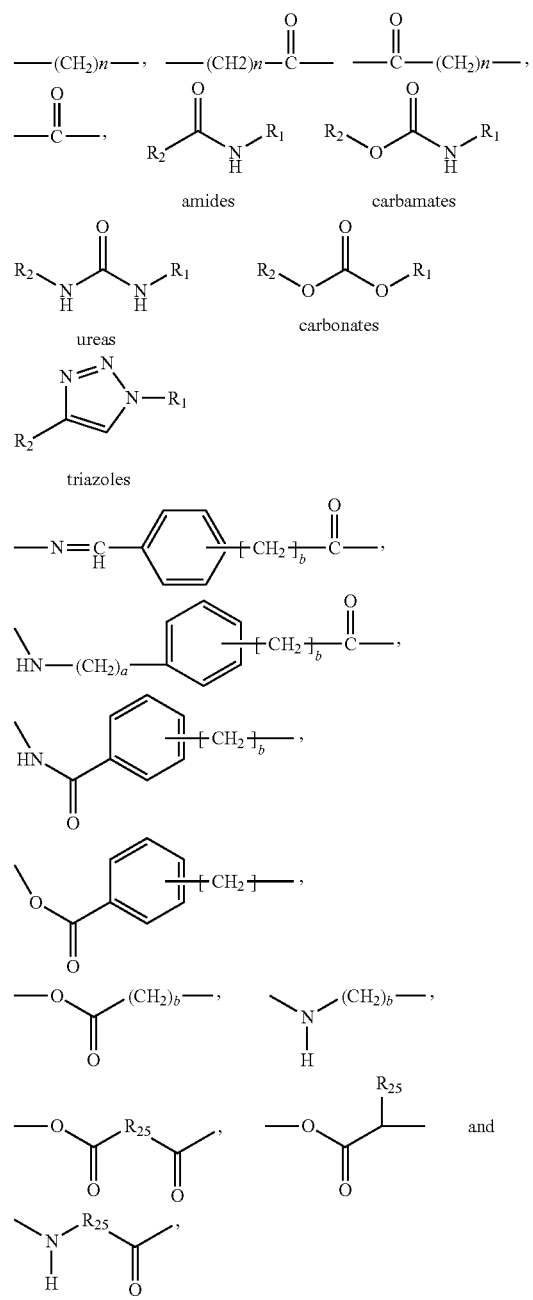

wherein:
n is 0 to 6, a is 0 to 3 and b is 0 to 3; and $R_{25}$ is selected from the group consisting of alkylene, alkenyl, and arylenyl.

A particular example of the present invention is a compound of Formula II:

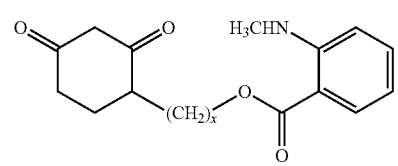

wherein x represents an integer from 1 to 10.

A further particular example of the present invention is a compound of Formula III:

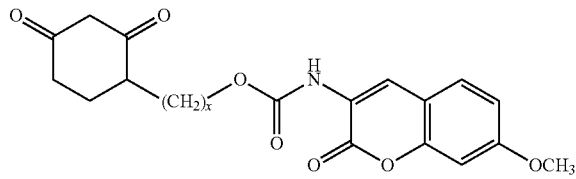

wherein x represents an integer from 1 to 10.

Other examples. Dimedone reacts with sulfenic acids because it has a very acidic and nucleophilic carbon ("an active methylene group") that is situated between two electron withdrawing groups (the two ketones in a 1,3 orientation). So, other compounds in addition to 1,3 diketones are useful as sulfenic acid traps. Some examples of such other compounds are shown in the scheme below. Particularly, other cyclic molecules like Meldrum's acid or barbituric acid are also useful agents that are not 1,3 diketones (one a diester and the other a diamide), yet are also useful as sulfenic acid traps. Linkages are carried out in accordance with techniques that will be apparent to persons skilled in the art. Also, this reactivity is not limited to active methylene compounds in rings. Open chain molecules like diethyl malonate and malodinitrile are also useful in carrying out the present invention. There are numerous combinations of functional groups that could be in the 1 and 3 positions to yield an active methylene group (ketones, esters, nitriles, aldehydes, and nitro groups are non-limiting examples thereof). Of interest, each of these different compounds may have a different rate profile with reaction with sulfenic acids. Generic structures are set forth at the bottom of the scheme below to exemplify minimal structures needed to react with a sulfenic acid (bearing in mind that some potential compounds that could react with sulfenic acids (like malodinitrile) would be eliminated as they do not have any good places to add a label).

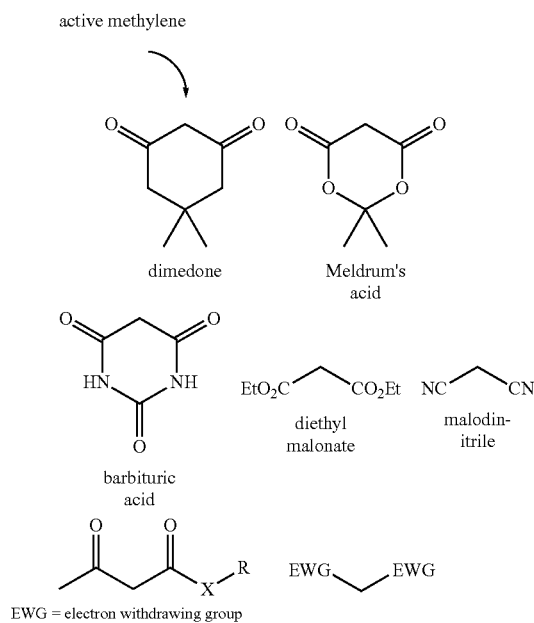

Formulations and administration. The term "active agent," as used herein, includes the pharmaceutically acceptable salts of the compounds described herein. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Active agents used to prepare compositions for the present invention may alternatively be in the form of a pharmaceutically acceptable free base of active agent. Because the free base of the compound is less soluble than the salt, free base compositions are employed to provide more sustained release of active agent to the target area. Active agent present in the target area which has not gone into solution is not available to induce a physiological response, but serves as a depot of bioavailable drug which gradually goes into solution.

The compounds of the present invention are useful as pharmaceutically active agents and may be utilized in bulk form. More preferably, however, these compounds are formulated into pharmaceutical formulations for administration. Any of a number of suitable pharmaceutical formulations may be utilized as a vehicle for the administration of the compounds of the present invention.

The compounds of the present invention may be formulated for administration for the treatment of a variety of conditions. In the manufacture of a pharmaceutical formulation according to the invention, the compounds of the present invention and the physiologically acceptable salts thereof, or the acid derivatives of either (hereinafter referred to as the "active compound") are typically admixed with, inter glia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.5% to 95% by weight of the active compound. One or more of each of the active compounds may be incorporated in the formulations of the invention, which may be prepared by any of the well-known techniques of pharmacy consisting essentially of admixing the components, optionally including one or more accessory ingredients.

The formulations of the invention include those suitable for oral, rectal, topical, buccal (e.g., sub-lingual), parenteral (e.g., subcutaneous, intramuscular, intradermal, or intravenous) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above).

In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration conveniently comprise sterile aqueous preparations of the active compound, which preparations are preferably isotonic with the blood of the intended recipient. These preparations may be administered by means of subcutaneous, intravenous, intramuscular, or intradermal injection. Such preparations may conveniently be prepared by admixing the compound with water or a glycine buffer and rendering the resulting solution sterile and isotonic with the blood.

Formulations suitable for topical application to the skin preferably take the form of an ointment, cream, lotion, paste, gel, spray, aerosol, or oil. Carriers which may be used include vaseline, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3:318 (1986)) and typically take the form of an optionally buffered aqueous solution of the active compound. Suitable formulations comprise citrate or bis\tris buffer (pH 6) or ethanol/water and contain from 0.01 to 0.2M active ingredient.

Antitumor/anticancer or other therapeutic Uses. When labeled with an antitumor or other pharmaceutical agent, compounds of the present invention are useful in the treatment of cancer or other diseases as noted above. For such purposes the compounds may be provided as a pharmaceutical formulation in a suitable pharmaceutical carrier, for example an aqueous carrier such as sterile pyrogen-free water or saline solution. The pharmaceutical formulation may be administered to a subject (e.g., a human subject, or other mammalian subject such as a dog, cat, or monkey for veterinary purposes) afflicted with a cancer as noted above by any suitable means, typically parenterally (e.g., intraveneous, subcutaneous, intraperitoneal injection, etc.) in any suitable amount (from about 0.001 mg/kg, 0.01 mg/kg, 0.1 mg/kg or 0.3 mg/kg; to about 0.3 mg/kg, 0.5 mg/kg, 1.0 mg/kg, or 10.0 mg/kg, or more).

The present invention is explained in greater detail in the non-limiting Experimental section set forth below.

Experimental

In order to provide a new tool for identifying and isolating sulfenic acid-containing proteins and peptides, we designed and synthesized a functionalized derivative of the dimedone-like compound 1,3-cyclohexadione (3 in Scheme 1), followed by linkage of the alcohol function to two different fluorophore groups, isatoic acid and 7-methoxycoumarin to yield fluorescent, sulfenic acid-reactive compounds (6 and 7 in Scheme 3). Data presented herein confirm the utility of these reagents in specifically and rapidly labeling sulfenic acid groups in proteins. Further, the synthetic methods should be generally useful for linking other types of fluorescent or affinity tags to sulfenic acid-containing proteins for analysis and isolation.

Synthesis. As preliminary biochemical results revealed that 1,3-cyclohexadione reacts in a similar manner to dimedone, the protected version of 1,3-cyclohexadione, 3-ethoxy-2-cyclohexen-1-one (1, Scheme 1), was chosen as the initial starting material for the preparation of fluorescently-labeled probes. Starting with 1, which readily hydrolyzes to 1,3-cyclohexadione under acidic conditions,

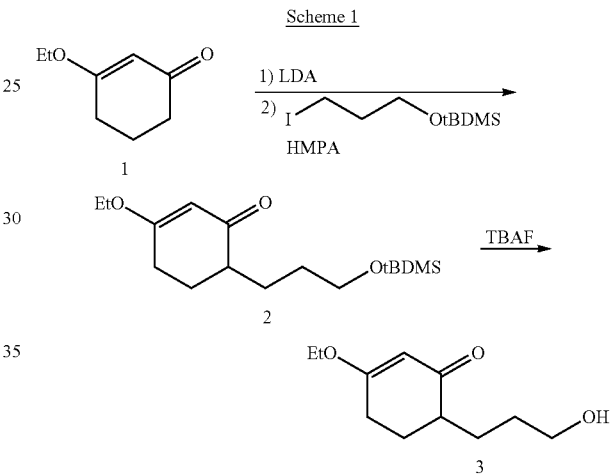

removes any synthetic complications from the highly acidic ($pk_a$=5.15) (12) active methylene group of dimedone. Alkylation of the anion of commercially available 3-ethoxy-2-cyclohexen-1-one with t-butyldimethylsilyl (TBDMS) (13)-protected 3-iodo-1-propanol yields 2 (51% yield, Scheme 1). Treatment of 2 with tetra-n-butylammonium fluoride (TBAF) removes the silyl group to give the alcohol (3, 100%, Scheme 1). The alcohol group of 3 provides an attachment site for the fluorescent groups.

Condensation of 3 with N-methylisatoic anhydride yields the protected 1,3-cyclohexadione derivative (4, 45%, Scheme 2). Heating 7-methoxycoumarin-3-carboxylic acid in the presence of diphenyl phosphorazidate (DPPA) and 3 gives the protected derivative (5, 50%, Scheme 2), presumably through the Curtius rearrangement of the acyl azide to the isocyanate followed by condensation of 3. Treatment of 4 and 5 with aqueous HCl cleanly produces 3-(2,4-dioxocyclohexyl)propyl 2-(methylamino)benzoate (6, DCP-MAB, Scheme 3) and 3-(2,4-dioxocyclohexyl)propyl 7-methoxy-2-oxo-2H-chromen-3-ylcarbamate (7, DCP-MCC, Scheme 3) in 96 and 59% yield, respectively. Both the ester linkage of 6 and the carbamate linkage of 7 appear generally stable to these acidic deprotection conditions.

Scheme 2

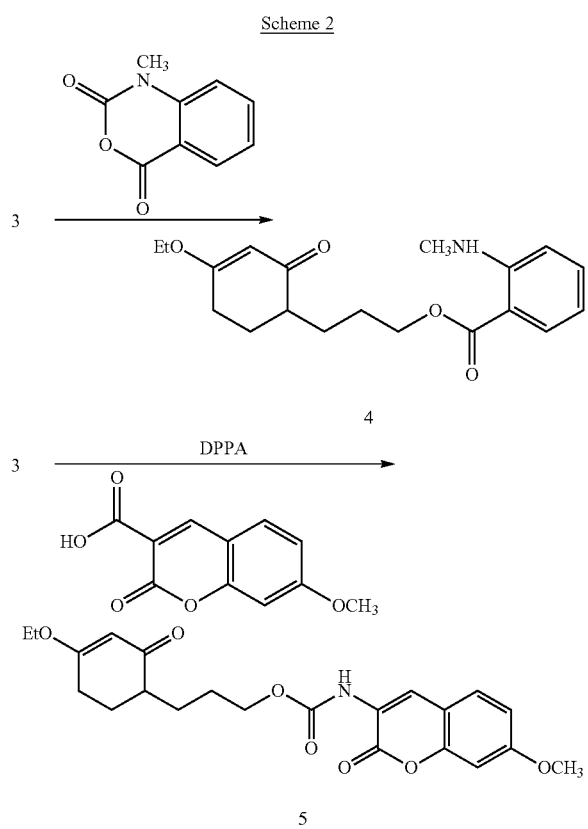

Scheme 3

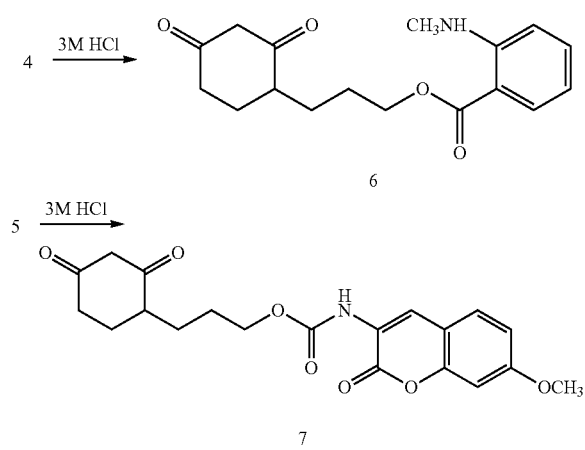

Reactivity of new compounds toward cysteine sulfenic acids in proteins. To test for the reactivity of 6 and 7 toward protein sulfenic acids, a mutant, cysteine-dependent peroxidase enzyme was used in which the oxidized, sulfenic acid form of the cysteinyl redox center is stabilized, yet accessible (the C165S mutant of AhpC from *Salmonella typhimurium*, a peroxiredoxin) (3, 9, 14). Both compounds, dissolved initially in dimethylsulfoxide and diluted 20-fold to a final concentration of 5 mM in aqueous, neutral pH buffer, gave covalent adducts with the sulfenic, but not sulfinic or sulfonic, acid forms of the peroxidase (Scheme 4).

The thiol group of the reduced protein and the oxidized, disulfide-bonded form of wild type AhpC were also unreactive toward these compounds, as confirmed by electrospray ionization mass spectrometry (ESI-MS) of the ammonium bicarbonate-washed Scheme 4

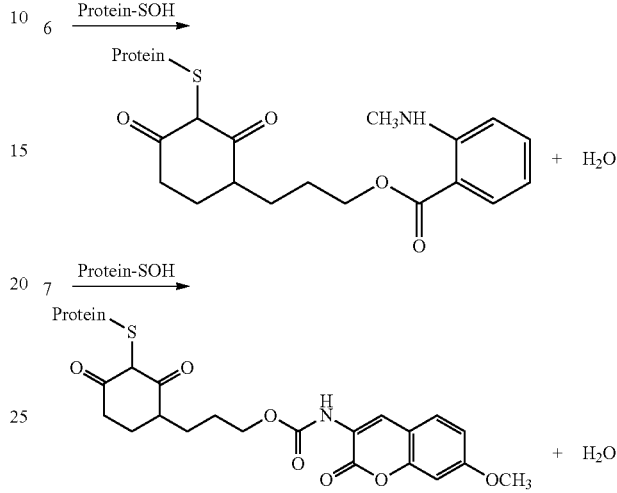

washed proteins following incubations with the labeling agents (FIG. 1 and data not shown). As illustrated in FIG. 1 and summarized in Table 1, mass spectrometry results were completely consistent with the expected reactivity and products generated with the sulfenic acid-containing protein using dimedone, 1,3-cyclohexadione and our two new labeling agents (6 and 7). Where sulfenic acid and hence adduct generation was substoichiometric due to the rapid addition of excess hydrogen peroxide (converting much of the enzyme to the sulfinic and perhaps sulfonic acid forms), additional peaks for thiol (unoxidized), and hyperoxidized ($R-SO_2^-$ and $R-SO_3^-$) protein were observed (FIG. 1). Under the conditions used, the sulfenic acid form of the protein either reacts with the reagent or is further oxidized during the workup or analysis of the sample, and is therefore not observed. In a subsequent experiment

TABLE 1

Observed and predicted masses of products following sulfenic acid-directed labeling of target protein (C165S AhpC).

| Reagent | Observed increase in mass of product compared with R—SH form[a] | Predicted additional mass of product[b] |
| --- | --- | --- |
| 1,3-cyclohexadione | 109.2 | 110.1 |
| DCP-MAB (6) | 300.7 | 301.4 |
| DCP-MCC (7) | 384.5 | 385.4 |
| Dimedone | 137.3 | 138.2 |

[a]Mass from electrospray ionization mass spectrometry on a Micromass Quattro II triple quadrapole mass spectrometer of the modified product from which was subtracted the mass for the oxidized sulfinic acid product ($R-SO_2^-$) present in each sample, adjusted 32 amu for the two oxygen atoms.
[b]Mass of labeling agent minus 2.016 for loss of hydrogens during adduct formation.

where sulfenic acid formation was measured at ~73%, an equivalent amount of 6 or 7 (74 and 67%, respectively) was incorporated into the protein as observed by ESI-MS (Table 1).

Figure 2:
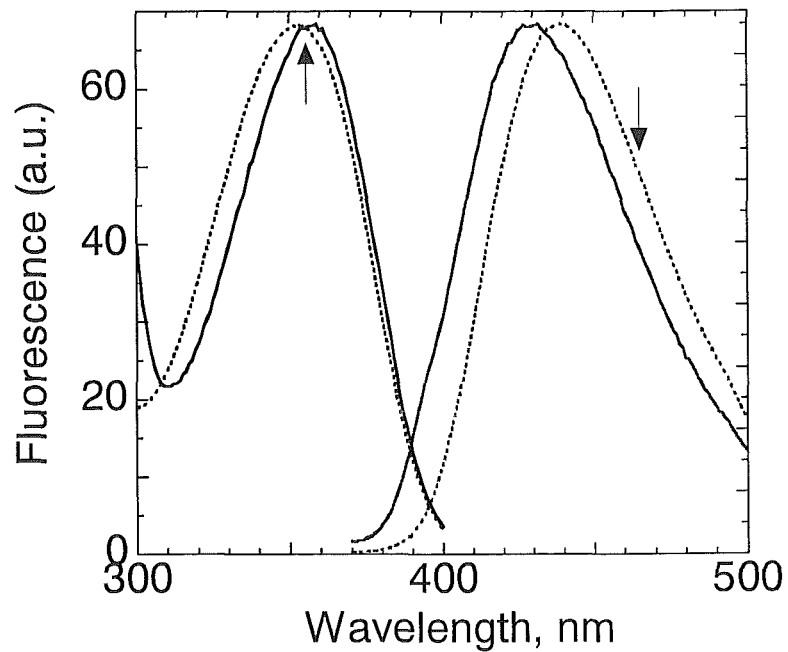
FIG. 2. Fluorescence spectra of 3-(2,4-dioxocyclohexyl) propyl 2-(methylamino)benzoate (DCP-MAB, compound 6) before (solid) and after (dotted) reaction with cysteine sulfenic acid-containing protein. Labeled C165S AhpC was prepared as described in the Experimental Section with the cysteine sulfenic acid form of the protein incubated anaerobically with 5 mM of 6 for 60 min, then washed free of the unreacted reagent and buffer components into a final buffer of 50 mM Tris-HCl at pH 8 using an Apollo concentrator. The absorbance at 347 nm of this sample was 0.14, and the fluorescence measurements were taken using a semi-micro cuvette with the 0.4 mm cuvette width directed toward the excitation beam and the 1.0 mm internal width directed toward the emission detector at 90°. Emission scans (370 to 500 nm) were collected at an excitation wavelength of 353 or 357 nm, respectively, for the free and protein-bound 6, and excitation scans (250 to 400 nm) were collected at an emission wavelength of 440 or 430 nm, respectively. For subsequent experiments to determine the rates of reaction of cysteine sulfenic acid-containing C165S AhpC with 6, excitation and emission wavelengths were set at 357 and 464 nm, respectively (shown by arrows in the figure).

The fluorescence properties of 7 ($\lambda_{ex,max}$=341 nm and $\lambda_{em,max}$=414 nm) were unchanged upon reaction with the cysteine sulfenic acid, while small shifts in both the excitation and emission wavelength maxima were observed upon adduct formation with 6, the isatoic acid derivative (from $\lambda_{ex,max}$=353 nm to $\lambda_{ex,max}$=357 nm, and from $\lambda_{em,max}$=440 nm to $\lambda_{em,max}$=430 nm, FIG. 2). Though small, these spectral changes allow one to directly and continuously monitor the fluorescence changes as 6 reacts with the sulfenic acid-containing protein. In 45 mM potassium phosphate buffer at pH 7 and 23° C., the second order rate constant for the reaction of 6 with the R—SOH of the C165S mutant of AhpC is ~500 $M^{-1}$ $min^{-1}$ (data not shown). Protein adduct amounts assessed by ESI-MS analyses of the intact proteins indicate approximately equal labeling of the protein with the two reagents when 1:1 mixtures of the 6 and 7 are added, suggesting similar rates of reaction for these two compounds. While it is unlikely that all protein sulfenic acids react with these compounds at the same rate due in part to varying accessibility of the reactive group, it is probable that, under denaturing and anaerobic conditions, reaction rates will be similar to those with the model protein sulfenic acid.

Specificity of fluorescent, cyclohexadione-derived regents toward sulfenic acids in proteins. The known reactivity of the nucleophilic center of dimedone is toward cysteine sulfenic acids and aldehydes (15, 16). Amines have also been shown to condense with dimedone (17). As described above, control reactions of thiol, disulfide or hyperoxidized forms of AhpC (wild type or C165S) demonstrated their lack of reactivity toward 6, 7 and dimedone based on the lack of ESI-MS-detectable adduct formation. To test for general cross-reactivity of these reagents with other oxidized sulfur-containing functional groups, we tested the reactivity of dimedone, as a model reagent, with a S-nitrosothiol and two sulfoxides. Dimedone fails to react with S-nitrosoglutathione (GSNO) as judged by absorbance spectroscopy over one hour at room temperature. Nuclear magnetic resonance (NMR), spectroscopic and chemical isolation experiments show that dimedone does not react with aqueous solutions of either dimethyl sulfoxide or methionine sulfoxide (data not shown).

As reported, dimedone demonstrates reactivity with both aldehydes and amines (16, 17). Control reactions show that dimedone reacts with butyraldehyde in the presence of piperidine at 50° C. in aqueous ethanol but fails to react with the same aldehyde at room temperature in the absence of base. In addition, while dimedone condenses with benzylamine to form an imine in organic solvent, no reaction occurs in aqueous ethanol. The failure of 6 and 7 to react with either reduced or oxidized wild type or reduced C165S AhpC proteins also indicates that these compounds do not react with protein amine groups under these conditions. Taken together, these results demonstrate the relative specificity of the reaction of these compounds for sulfenic acids in proteins in aqueous buffers.

Conclusions. Functionalization of 1,3-cyclohexadione derivatives with an alcohol group and subsequent coupling to fluorophores has successfully generated two sulfenic acid-reactive compounds that specifically incorporate a fluorescent label into a sulfenic acid-containing model protein. Compounds such as these should prove useful in tagging protein sulfenic acids for their detection and isolation from complex protein mixtures in the future.

Experimental Section.

3-Ethoxy-6-(3-t-butyldimethylsilyloxypropyl)cyclohex-2-enone (2). To a lithium diisopropylamide (LDA) solution [prepared from diisopropylamine (3.82 mL, 27 mmol) and nBuLi (7.26 mL of a 2.5M solution in hexanes, 18 mmol) in tetrahydrofuran (THF, 12 mL) at 0° C.] at −78° C. was added 3-ethoxy-2-cyclohexen-1-one (2.64 mL, 18 mmol) in THF (6 mL), dropwise, over 40 min. After stirring for an additional 30 min at −78° C., hexamethyl phosphoramide (HMPA, 3.16 mL, 18 mmol) was added followed by the dropwise addition of 3-iodo-1-tert -butyldimethylsiloxypropane (5.45 g, 18 mmol) in THF (8 mL). The resultant mixture was allowed to warm to rt, stirred for 6 h and then quenched by the addition of water (10 mL). The reaction mixture was then partitioned between dichloromethane (DCM, 100 mL) and sat. $NH_4Cl$ (40 mL). The aqueous phase was extracted with DCM (3×50 mL), the organic phases combined and washed with brine (50 mL), dried over anhydrous $MgSO_4$ and reduced to dryness. The resultant syrup was purified by flash column chromatography (hexanes/EtOAc 8/2) to yield 2 as a pale yellow oil (2.92 g, 51.2%). Rf 0.21 (hexanes/EtOAc 8/2); $^1$H NMR (300 MHz, $CDCl_3$) δ 5.26 (1H, s), 3.83 (2H, q, J=7.0 Hz), 3.59 (1H, t, J=6.5 Hz), 3.58 (H, t, J=6.5 Hz), 2.38 (2H, t, J=6.2 Hz), 2.20-1.99 (2H, m), 1.85-1.35 (5H, m), 1.31 (3H, t, J=7.0 Hz), 0.84 (s, 9H), 0.00 (s, 6H); $^{13}$C NMR (75 MHz, $CDCl_3$) δ 201.6, 176.7, 102.3, 64.2, 63.4, 45.0, 30.5, 28.0, 26.4, 26.0 (×2), 18.4, 14.2, −5.2.

3-Ethoxy-6-(3-hydroxypropyl)cyclohex-2-enone (3). To a solution of 2 in THF (20 mL) was added TBAF (23.2 mL of a 1.0 M solution in THF, 23.2 mmol) and $NEt_3$ (3.2 mL, 23.2 mmol). After stirring at rt for 2 h, the reaction was quenched by the addition of water (20 mL) and sat. $NH_4Cl$ (20 mL). The mixture was extracted with DCM (3×80 mL) and the combined organic phases dried over anhydrous $MgSO_4$ and reduced to dryness. The resultant syrup was purified by flash column chromatography with gradient elution (DCM/diethyl ether 1/1 to 3/7) to yield 3 as a pale yellow oil (1.85 g, 100%). Rf 0.37 (hexanes/EtOAc/MeOH 6/3/1); NMR (300 MHz, $CDCl_3$) δ 5.32 (1H, s), 3.89 (2H, q, J=7.1 Hz), 3.64 (2H, t, J=6.2 Hz), 2.44 (2H, 2d, J=7.1 Hz), 2.24 (1H, m), 2.06 (1H, m), 1.92-1.49 (5H, m), 1.36 (3H, t, J=7.1 Hz); $^{13}$C NMR (75 MHz, $CDCl_3$) δ 202.0, 177.2, 102.3, 64.4, 62.6, 44.9, 30.3, 28.4, 26.8, 25.8, 14.3.

3-(4-Ethoxy-2-oxocyclohex-3-enyl)propyl 2-(methylamino)benzoate (4). Alcohol 3 (180 mg, 0.89 mmol), $NEt_3$ (0.56 mL) and catalytic DMAP were added to a solution of N-methylisatoic anhydride (220 mg, 0.89 mmol) in dry DMF (2.0 mL) at rt. After stirring overnight, the solution was warmed to 65° C. for 3 h. After cooling to rt, water was added and this mixture was extracted with ethyl acetate (5×50 mL). The combined organic layers were washed with brine, dried over $Na_2SO_4$, filtered, and evaporated to give the crude product, which was purified by flash column chromatography to afford 87.0 mg (45% yield) of 4 as a white solid: $^1$H NMR (300 MHz, $CDCl_3$) δ 7.85 (1H, m), 7.33 (1H, m), 6.56 (2H, m), 5.27 (1H, s), 4.22 (2H, t, J=5.2 Hz), 3.85 (2H, q, J=7.0 Hz), 2.86 (3H, s), 2.39 (2H, t, J=5.3 Hz), 2.04-1.41 (7H, m), 1.31 (3H, t, J=7.0 Hz); $^{13}$C NMR (75 MHz, $CDCl_3$) δ 201.1, 176.8, 168.7, 151.7, 134.7, 131.7, 115.0, 111.3, 110.6, 102.5, 101.9, 64.7, 64.5, 64.3, 44.9, 30.0, 28.2, 26.6, 26.5, 26.4, 14.3; ESI MS m/z 354 ($M^+$+$Na^+$).

3-(4-Ethoxy-2-oxocyclohex-3-enyl)propyl-7-methoxy-2-oxo -2H-chromen-3-ylcarbamate (5). A solution of 7-methoxy-3-carboxycoumarin (335 mg, 1.5 mmol), $NEt_3$ (1.05 mL, 7.6 mmol) and DPPA (0.36 mL, 1.7 mmol) in benzene (15 mL) was stirred at 65° C. for 4 h. A solution of 3 (260 mg, 1.3 mmol) in benzene (2 mL) was then added and the mixture stirred at 65° C. for 16 h. Upon cooling, water (40 mL) was added and the mixture extracted with DCM (3×40 mL). The combined organic phases were washed with sat. $NaHCO_3$ (30 mL), brine (30 mL), dried over anhydrous $MgSO_4$ and reduced to dryness. The resultant solid was purified by flash column chromatography (×2, gradient elution with DCM/EtOAC (8/2) to DCM/EtOAc/MeOH (8/1/1), and then DCM/MeOH (9/1)) to yield 5 as an off-white solid (270 mg, 49.5%). Rf 0.63 (hexanes/EtOAc 1/2); Mp. 131-134° C.; $^1$H NMR (300 MHz, CDCl$_3$) δ 8.22 (1H, s), 7.34 (2H, m), 6.84 (1H, dd, J=8.6 Hz, 2.4 Hz), 6.79 (1H, d, J=2.4 Hz), 5.29 (1H, s), 4.18 (2H, t, J=6.3 Hz), 3.85 (2H, 2q, J=7.0 Hz), 3.82 (3H, s), 2.42 (2H, 2d, J=7.1 Hz), 2.22 (1H, m), 2.08 (1H, dq, J=14.2 Hz, 5.0 Hz), 1.94-1.85 (1H, m), 1.78-1.66 (3H, m), 1.52-1.42 (1H, m), 1.33 (3H, t, J=7.0 Hz); $^{13}$C NMR (75 MHz, CDCl$_3$) δ 201.0, 176.9, 161.1, 158.9, 153.6, 151.3, 128.4, 122.0, 121.9, 113.3, 113.2, 102.4, 100.8, 66.0, 64.4, 55.9, 44.9, 28.3, 26.6 (×2), 26.2, 14.3; ESI MS m/z 438 (M$^+$+Na$^+$).

3-(2,4-Dioxocyclohexyl)propyl 2-(methylamino)benzoate (DCP-MAB, compound 6). Compound 4 was stirred in a mixture of THF/3N HCl (1/1) at rt for 3 h and the mixture was concentrated. The crude product was washed with EtOAc/hexane/MeOH (1/2/0.5) to afford 6 as a white solid: $^1$H NMR (300 MHz, CDCl$_3$) δ 7.83 (1H, m), 7.34 (1H, m), 6.55 (2H, m), 4.22 (2H, t, J=6.3 Hz), 3.60 (2H, m), 2.84 (3H, s), 2.52-1.50 (9H, m); $^{13}$C NMR (75 MHz, CDCl$_3$) δ 204.3, 203.8, 168.6, 151.6, 134.9, 131.7, 131.5, 115.2, 111.6, 110.5, 64.1, 58.4, 49.1, 39.9, 30.1, 26.4, 26.0, 24.7; ESI MS m/z 326 (M$^+$+Na$^+$).

3-(2,4-Dioxocyclohexyl)propyl 7-methoxy-2-oxo-2H-chromen-3-ylcarbamate (DCP-MCC, compound 7). Compound 5 (240 mg, 0.58 mmol) was stirred in a mixture of THF/DCM (3/1 v/v, 4 mL) and 3N HCl (4 mL) for 1 hr. The reaction mixture was diluted with water (10 mL) and extracted with DCM (3×30 mL). The combined organic phases were dried over anhydrous MgSO$_4$ and reduced to dryness to yield the crude product, which was purified by flash column chromatography (EtOAc/acetone 4/1) to yield 7 as an off-white solid (133 mg, 59.4%). Rf 0.62 (hexanes/EtOAc/MeOH 6/3/1); Mp. 154-156° C.; $^1$H NMR (300 MHz, CDCl$_3$) δ 8.25 (1H, s), 7.42 (1H, s), 7.39 (1H, d, J=8.7 Hz), 6.88 (1H, dd, J=8.6 Hz, 2.1 Hz), 6.83 (1H, d, J=2.1 Hz), 4.23 (2H, t, J=6.5 Hz), 3.86 (3H, s), 3.44 (2H, d, J=5.1 Hz), 2.78-2.69 (1H, dt, J=16.4 Hz, 4.4 Hz), 2.67-2.51 (2H, m), 2.24-2.15 (1H, dq, J=14.1 Hz, 4.8 Hz), 2.03-1.95 (1H, m), 1.88-1.47 (6H, m); $^{13}$C NMR (75 MHz, CDCl$_3$) δ 204.2, 203.8, 161.2, 158.9, 153.5, 151.3, 128.4, 122.0, 121.8, 113.3, 113.2, 100.9, 65.6, 58.5, 55.9, 49.1, 39.9, 26.4, 25.7, 24.8; ESI MS m/z 410 (M$^+$+Na$^+$), 388 (M$^+$+H$^+$); CHN calc. for C$_{20}$H$_{21}$NO$_7$.0.5H$_2$O, C: 60.59; H: 5.61; N: 3.53. found C, 61.31, H: 5.56, N: 3.48.

Generation of pure, sulfenic acid-containing C165S AhpC. The C165S mutant of AhpC was expressed in bacteria and purified in the presence of 5 mM 1,4-dithiothreitol (added to all buffers) essentially as described previously (9). Purification of wild type AhpC was also carried out as previously described (10). For generation of the sulfenic acid form of C165S AhpC, thawed enzyme in 25 mM phosphate buffer at pH 7, containing 1 mM EDTA, was washed free of the dithiothreitol and transferred into fresh buffer using a PD-10 column (Amersham Biosciences), and pooled fractions were transferred to an anerobic cuvette. The protein solution (160 nmol in 0.60 mL) was made anaerobic by repeated cycles of argon and vacuum over about 30 min, then rapidly titrated with 11 mM hydrogen peroxide to give a maximal absorbance signal at ~367 nm for the sulfenate anion as described previously (3, 4). In subsequent experiments, optimal sulfenic acid formation was observed by adding and mixing the hydrogen peroxide much more slowly (additions of about 0.05 eq and thorough mixing every ~1 min) and quantitating the sulfenic acid formed using a freshly-prepared 2-nitro-5-thiobenzoate (TNB) solution (0.28 mL) and a 60 μL aliquot of the protein removed anaerobically from the cuvette (3, 4). Using this method, ~73% of the protein was converted to the sulfenic acid form after addition of 1.08 eq of hydrogen peroxide. Protein was kept in the anaerobic cuvette at room temperature for several hours before conducting experiments with no loss in sulfenic acid content.

Labeling of sulfenic acid-containing C165S AhpC for spectral and mass spectrometric analysis. The pure, oxidized enzyme (32 μL, 6 nmol each) from the anaerobic cuvette was added to argon-flushed 500 μL Eppendorf tubes containing the compound of choice (either dimethylsulfoxide alone, or dimethylsulfoxide into which dimedone, 1,3-cyclohexanedione, 6 or 7 had been dissolved) to give a final concentration of 5 mM for the added reagent in final volumes of 50 μL, and the tubes were flushed again with argon before closing. Other redox forms of C165S AhpC or the wild-type enzyme were also tested for reactivity with one or more of these four compounds. Approximate 100 mM stock solutions of 6 or 7 in dimethylsulfoxide were standardized using expected extinction coefficients of 5,700 or 25,000 M$^{-1}$ cm$^{-1}$, respectively, for the esterified isatoic acid conjugate or the methoxycoumarin conjugate in methanol (11). Samples were incubated at room temperature for 60 min, then transferred to Apollo ultrafiltration devices (30K cutoff, Orbital Biosciences, Topsfield, Mass.), washed with 5.5 mL 10 mM ammonium bicarbonate and reconcentrated to about 50 μL, for a total of four washes (>10$^8$-fold dilution of the initial small molecule components).

Mass spectrometric and spectral analyses of adducts with the sulfenic acid-containing form of C165S AhpC. For mass spectrometric analyses, 60 μL of the ammonium bicarbonate buffer containing 1-2 nmol of labeled or unlabeled protein was submitted to the Mass Spectrometer Facility at Wake Forest University School of Medicine for infusion analysis on a Micromass Quattro II triple quadrupole mass spectrometer equipped with a Z-spray source. Just prior to analysis, samples were diluted 1:1 with acetonitrile and 1% formic acid was added. The data were processed and analyzed using MassLynx Version 3.5.

Labeled protein samples washed (with Apollo concentrators) into potassium phosphate or ammonium bicarbonate buffers were also analyzed for their UV-visible spectroscopic and fluorescence properties using a Beckman DU7500 diode array spectrophotometer or a SLM Aminco-Bowman Series 2 luminescence spectrophotometer, respectively. By comparison with the reported extinction coefficients for each of the free reagents in methanol (5,700 M$^{-1}$ cm$^{-1}$ for esterified isatoic acid, and 25,000 M$^{-1}$ cm$^{-1}$ for methoxycoumarin) (11), the free and presumably protein-bound reagents in neutral pH phosphate buffer exhibited average extinction coefficients of ~4,250 and ~20,900 M$^{-1}$ cm$^{-1}$, respectively, for 6 and 7. These measured values were subsequently used to standardize 6 and 7 and to estimate the labeled protein concentrations.

Analysis of the rate of reaction of the cysteine sulfenic acid-containing C165S AhpC with DCP-MAB (6), and of other potentially reactive compounds with dimedone. To 10 nmol of sulfenic acid-containing C165S AhpC in 50 mM potassium phosphate buffer at pH 7.0 was added 6 (from a 119 mM stock solution in dimethyl sulfoxide) at final concentrations of 0.6 to 2.4 mM and a total volume of 0.5 mL. Fluorescence descreases were monitored at 23° C. using excitation and emission wavelengths of 357 and 464 nm and slit widths of 4 and 16 nm, respectively. Both free and protein-bound DCP-MAB exhibit the same absorbance at this excitation wavelength, allowing the experiment to be conducted at high concentrations without complications due to the inner filter effect (A$_{357}$ of ~2 to 10). Fluorescence changes were monitored at 15 s to 2 min intervals until complete, and each first order rate constant was analyzed using Kaleidagraph (Synergy Software) and the equation:

$$y = A + Be^{-k_{obst}}$$

where y is the fluorescence value at a given time t, and A and B are the final fluorescence value (A) and amplitude of fluorescence change (B) parameters associated with the change, and k$_{obs}$ is the pseudo-first order rate constant (with A, B and $k_{obs}$ supplied by the fit to the data). The slope of the secondary plot of the observed rate constant, $k_{obs}$, versus concentration of 6 was taken as the second order rate constant for the reaction of 6 with the cysteine sulfenic acid-containing C165S mutant of AhpC.

In addition to the compounds described above, several additional compounds have been synthesized with fluorophore or biotin labels as described below.

Synthesis of a 1,3-cyclohexadione-fluorescein derivative. Condensation of commercial fluoresceinamine with p-nitrophenyl chloroformate gives a reactive carbamate that condenses with alcohol (3, Scheme 1) to produce a protected 1,3-cyclohexadione-fluorescein derivative (Scheme 5). Acidic deprotection of the enol ether group yields the desired probe in good yield (Scheme 5).

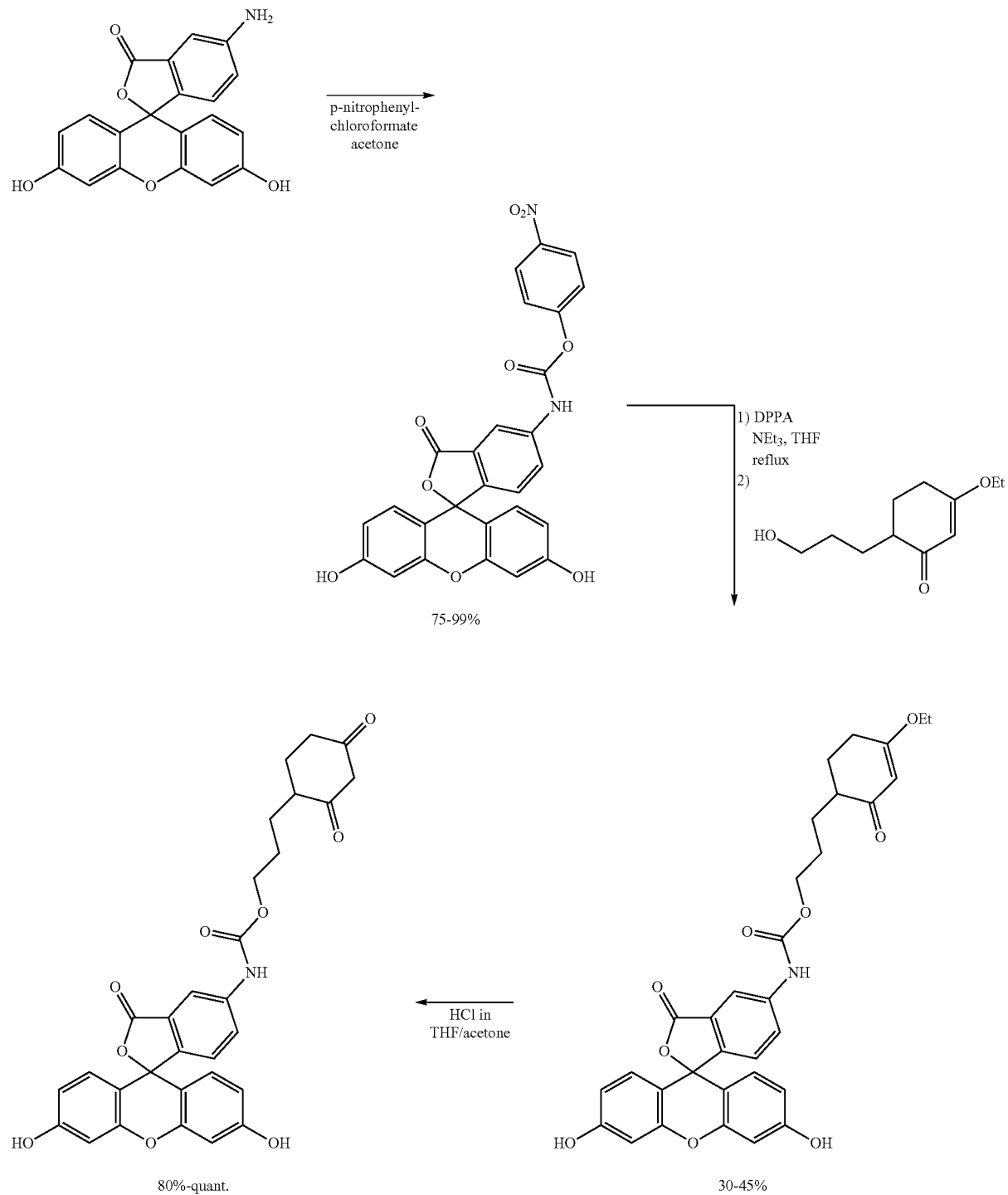

Scheme 5

Synthesis of a 1,3-cyclohexadione-biotin derivative. Standard coupling of commercial biotin using dicyclocarbodiimide (DCC) with alcohol (3, Scheme 1) gives a protected 1,3-cyclohexadione-biotin derivative (Scheme 6). Further acidic deprotection of the enol ether group yields the desired biotin-based probe in good yield (Scheme 6).

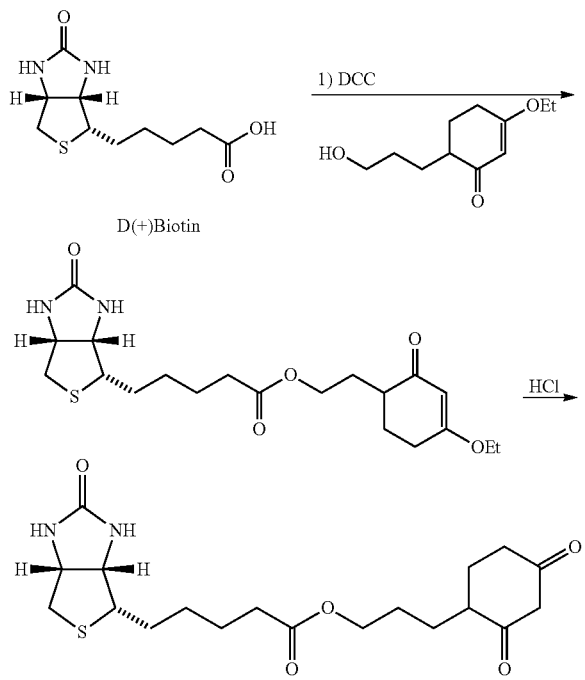

REFERENCES

1. Claiborne, A., Yeh, J. I., Mallett, T. C., Luba, J., Crane, E. J., 3rd, Charrier, V., and Parsonage, D. (1999) Protein-sulfenic acids: diverse roles for an unlikely player in enzyme catalysis and redox regulation, *Biochemistry* 38, 15407-15416.
2. Poole, L. B., Karplus, P. A., and Claiborne, A. (2004) Protein sulfenic acids in redox signaling, *Annu. Rev. Pharmacol. Toxicol.* 44, 325-347.
3. Poole, L. B., and Ellis, H. R. (2002) Identification of cysteine sulfenic acid in AhpC of alkyl hydroperoxide reductase, *Methods Enzymol* 348, 122-136.
4. Poole, L. B. (2003) Measurement of protein sulfenic acid content, in *Curr. Prot. Toxicol.* (Maines, M. D., Ed.) pp 17.12.11-17.12.20, John Wiley & Sons, Inc., New York.
5. Allison, W. S. (1976) Formation and reactions of sulfenic acids in proteins, *Acc. Chem. Res.* 9, 293-299.
6. Willett, W. S., and Copley, S. D. (1996) Identification and localization of a stable sulfenic acid in peroxide-treated tetrachlorohydroquinone dehalogenase using electrospray mass spectrometry, *Chem Biol* 3, 851-857.
7. Detection of radioactively-labeled dimedone has also been used in the past, although this material is no longer commercially available and is prohibitively expensive to synthesize.
8. Saurin, A. T., Neubert, H., Brennan, J. P., and Eaton, P. (2004) Widespread sulfenic acid formation in tissues in response to hydrogen peroxide, *Proc Natl Acad Sci USA* 101, 17982-17987.
9. Ellis, H. R., and Poole, L. B. (1997) Roles for the two cysteine residues of AhpC in catalysis of peroxide reduction by alkyl hydroperoxide reductase from *Salmonella typhimurium*, *Biochemistry* 36, 13349-13356.
10. Poole, L. B., and Ellis, H. R. (1996) Flavin-dependent alkyl hydroperoxide reductase from *Salmonella typhimurium*. 1. Purification and enzymatic activities of overexpressed AhpF and AhpC proteins, *Biochemistry* 35, 56-64.
11. Haugland, R. P. (2002) *Handbook of fluorescent probes and research products*, Ninth ed., Molecular Probes, Inc.
12. The Merck Index, 12th Edition; Merck and Co., Inc: Whitehouse Station, 1996, p 548.
13. Abbreviations used are: TBDMS, t-butyldimethylsilyl; TBAF, tetra-n-butylammonium fluoride; amu, atomic mass units; THF, tetrahydrofuran; HMPA, hexamethylphosphoramide; DMAP, dimethyl amino pyridine; DPPA, diphenyl phosphorazidate; GSNO, S-nitrosoglutathione; NMR, nuclear magnetic resonance; LDA, lithium diisopropylamide; DCM, dichloromethane; ESI-MS, electrospray ionization mass spectrometry; NBD chloride, 7-chloro-4-nitrobenzo-2-oxa-1,3-diazole; DCP-MAB, 3-(2,4-dioxocyclohexyl)propyl 2-(methylamino)benzoate; DCP-MCC, 3-(2,4-dioxocyclohexyl)propyl 7-methoxy-2-oxo-2H-chromen-3-ylcarbamate
14. Ellis, H. R., and Poole, L. B. (1997) Novel application of 7-chloro-4-nitrobenzo-2-oxa-1,3-diazole to identify cysteine sulfenic acid in the AhpC component of alkyl hydroperoxide reductase, *Biochemistry* 36, 15013-15018.
15. Benitez, L. V., and Allison, W. S. (1974) The inactivation of the acyl phosphatase activity catalyzed by the sulfenic acid form of glyceraldehyde 3-phosphate dehydrogenase by dimedone and olefins, *J Biol Chem* 249, 6234-6243.
16. Vogel, A. I. (2005) Investigation and characterisation of organic compounds, in *Vogel's Textbook of Practical Organic Chemistry* (Furniss, B. S., Hannaford, A. J., Smith, P. W. G., and Tatchell, A. R., Eds.) pp 1259-1260, Pearson, Singapore.
17. Halpern, B., and James, L. B. (1964) Dimedone (5,5-dimethylcyclohexane-1,3-dione) as a protecting agent for amino groups in peptide synthesis, *Aust. J. Chem.* 17, 1282-1287.

The foregoing is illustrative of the present invention, and is not to be construed as limiting thereof. The invention is defined by the following claims, with equivalents of the claims to be included therein.

That which is claimed is:

1. A method of detecting a sulfenic acid containing target compound, comprising:
   contacting a compound with a target compound; and then detecting the presence or absence of binding of said compound to said target compound;
   the presence of binding indicating said target compound is a sulfenic acid containing target compound;
   wherein said compound is a compound of Formula I:

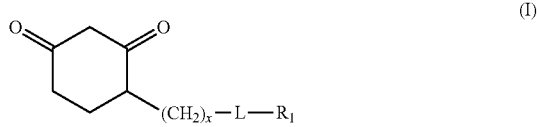

wherein:
   $R_1$ is a label selected from the group consisting of biotin, fluorophores, antigens, porphyrins, radioactive isotopes and anti-tumor agents;

L is present or absent and when present is a linking group; and x represents an integer from 1 to 10;

or a pharmaceutically acceptable salt thereof.

2. The method of claim 1, wherein the label is selected from the group consisting of biotin, fluorophores, antigens, porphyrins, and radioactive isotopes.

3. The method of claim 1, wherein said label is a fluorophore.

4. The method of claim 1, wherein said target compound is a protein.

5. The method of claim 1 wherein said compound is selected from the group consisting of:

(a) a compound of Formula II:

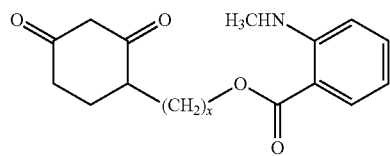

wherein x represents an integer from 1 to 10; and (b) a compound of Formula III:

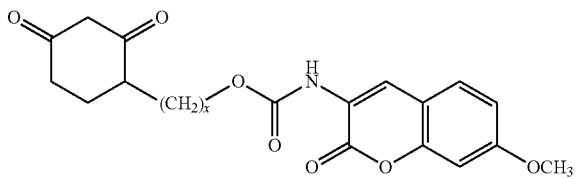

wherein x represents an integer from 1 to 10.

6. A method of identifying sulfenic acids in a protein, comprising:

applying a compound to said protein, and then detecting the presence or absence of binding of said compound to said protein, the presence of binding indicating the presence of sulfenic acids in said protein;

wherein said compound is a compound of Formula I:

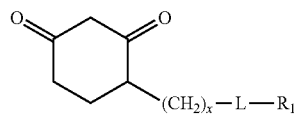

wherein:

R₁ is a label selected from the group consisting of biotin, fluorophores, antigens, porphyrins, radioactive isotopes and anit-tumor agents;

L is present or absent and when present is a linking group; and x represents an integer from 1 to 10;

or a pharmaceutically acceptable salt thereof.

7. The method of claim 6, wherein the label is selected from the group consisting of biotin, fluorophores, antigens, porphyrins, and radioactive isotopes.

8. The method of claim 6, wherein said label is a fluorophore.

9. The method of claim 6 wherein said compound is selected from the group consisting of:

(a) a compound of Formula II:

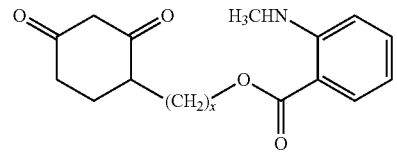

wherein x represents an integer from 1 to 10; and (b) a compound of Formula III:

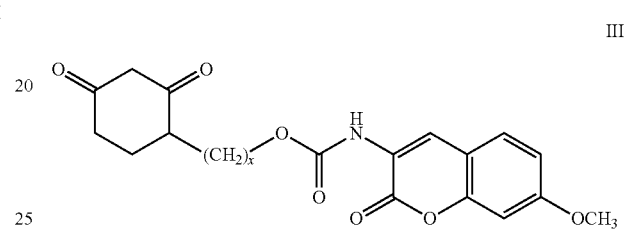

wherein x represents an integer from 1 to 10.

10. A method for monitoring oxidative damage comprising:

reacting a compound with a protein, a mixture of proteins, a cell lysate, intact cells or permeabilized cells comprising cysteine residues;

detecting the presence of binding indicating said protein, mixture of proteins, cell lysate, intact cells or permeabilized cells contain a sulfenic acid;

wherein an increase in binding of said compound to said protein, mixture of proteins, cell lysate, intact cells or permeabilized cells as compared to corresponding control said protein, mixture of proteins, cell lysate, intact cells or permeabilized cells prior to said oxidative damage indicates oxidative damage to said protein, mixture of proteins, cell lysate, intact cells or permeabilized cells;

wherein said compound is a compound of Formula I:

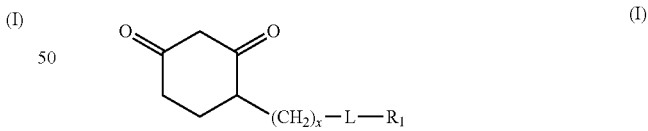

wherein:

R₁ is a label selected from the group consisting of biotin, fluorophores, antigens, porphyrins, radioactive isotopes and anti-tumor agents;

L is present or absent and when present is a linking group; and x represents an integer from 1 to 10;

or a pharmaceutically acceptable salt thereof.

11. The method of claim 10, wherein the label is selected from the group consisting of biotin, fluorophores, antigens, porphyrins, and radioactive isotopes.

12. The method of claim 10, wherein said label is a fluorophore.

13. The method of claim 10 wherein said compound is selected from the group consisting of:
   (a) a compound of Formula II:
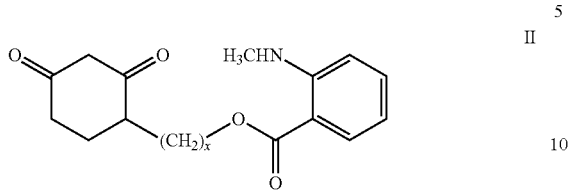
II
wherein x represents an integer from 1 to 10; and
   (b) a compound of Formula III:
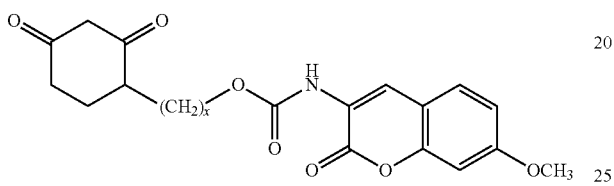
III
wherein x represents an integer from 1 to 10.
* * * * *

UNITED STATES PATENT AND TRADEMARK OFFICE
CERTIFICATE OF CORRECTION

PATENT NO.       : 8,841,132 B2
APPLICATION NO.  : 13/920989
DATED            : September 23, 2014
INVENTOR(S)      : Poole et al.

Page 1 of 1

It is certified that error appears in the above-identified patent and that said Letters Patent is hereby corrected as shown below:

In the Specification:
Column 12, Lines 5 and 30: Please correct: "bicarbonate-washed washed proteins"
    to read -- bicarbonate-washed proteins --

In the Claims:
Column 21, Line 58, Claim 6: Please correct "and anit-tumor agents;"
    to read -- and anti-tumor agents; --

Signed and Sealed this
Tenth Day of March, 2015

Michelle K. Lee
*Deputy Director of the United States Patent and Trademark Office*